United States Patent [19]
Norbury et al.

[11] Patent Number: 4,976,961
[45] Date of Patent: Dec. 11, 1990

[54] ENCAPSULATED COSMETIC MATERIALS AND PROCESS OF MAKING

[75] Inventors: Robert J. Norbury, Cottage Grove; Robert W. H. Chang, Roseville, both of Minn.

[73] Assignee: Minnesota Mining and Manufacturing Company, St. Paul, Minn.

[21] Appl. No.: 887,799

[22] Filed: Jul. 18, 1986

[51] Int. Cl.$^5$ .......................... A61K 9/50; A61K 9/66; B01J 13/18
[52] U.S. Cl. .................................... 424/401; 264/4.7; 424/408; 424/455; 424/462; 424/501; 428/402.21; 514/873; 514/963
[58] Field of Search .................... 264/4.7; 428/402.21; 252/174.13; 514/873, 963; 424/455, 462, 501, 401

[56] References Cited

U.S. PATENT DOCUMENTS

| | | | |
|---|---|---|---|
| 3,136,695 | 6/1964 | Tansey | 252/315.4 X |
| 3,210,248 | 10/1965 | Feldmann et al. | 514/873 X |
| 3,516,941 | 6/1970 | Matson | 428/402.21 |
| 3,705,102 | 12/1972 | Mast | 428/403 X |
| 3,798,179 | 3/1974 | Hellyer | 252/535 |
| 3,930,101 | 12/1975 | Vincent | 428/326 |
| 4,450,221 | 5/1984 | Terada et al. | 430/106.6 |

*Primary Examiner*—Richard D. Lovering
*Attorney, Agent, or Firm*—Donald M. Sell; Walter N. Kirn; Mark A. Litman

[57] ABSTRACT

The size of microcapsules having cosmetic emollient oils is increased by the inclusion of viscosity increasing agents with the oils.

22 Claims, No Drawings

ENCAPSULATED COSMETIC MATERIALS AND PROCESS OF MAKING

BACKGROUND OF THE INVENTION

1. Field of the Invention

The present invention relates to liquids or oils and especially cosmetic emollient oils in microcapsules for use in the application of materials to the skin or other surfaces and a process for increasing the size of microcapsules.

2. Background of the Art

It is fairly common to find encapsulated liquid materials in the marketplace. Technology has been available for many years to effectively provide microcapsules with liquid oleophilic ingredients. Representative processes are shown in U.S. Pat. Nos. 3,016,308 and 3,516,941. These patents disclose in situ polymerization reactions in which a hydrophobic oil phase is dispersed in an aqueous phase containing resin precursors, particularly aminoplast resin precursors (to form urea/aldehyde resins and the like). High shear agitation is used to keep the capsule size small. Addition of an acid catalyst initiates the polycondensation of the aminoplast precursors, resulting in the deposition of the aminoplast resin about the dispersed droplets of the oil phase. This produces the microcapsules.

Other polycondensation encapsulation techniques are shown in U.S. Pat. Nos. 3,429,827 and 4,000,087. These particular techniques are more limited in the classes of hydrophobic inner phases acceptable in the microcapsules because of reaction with the oil soluble monomer or poor solubility of the monomer in the desired hydrophobic phase.

U.S. Pat. NO. 3,930,101 teaches that, to be retained in the hydrophobic phase during high shear dispersion of a fluid particulate dispersion, it is necessary that the particulate be preferentially wetted by the hyrophobic phase. It is suggested to use suitable surfactants which adsorb to the particulate surface as a way to achieve the desired preferential wetting. It has, however, been recognized that, in the in situ polymerization of aminoplast resins method for encapsulation, the presence of surfactants interferes with the deposition of the aminoplast resin at the hydrophobic phase/water phase interface, giving poorly formed or leaky capsules. Similarly, oil soluble suspending agents could alter the wetting of many particulates. Since many of these materials contain carboxylate groups, exposure to highly acidic medias often converts them to carboxylic acid groups altering their adsorbability to the particulates.

U.S Pat. No. 4,450,221 teaches magnetic toners comprising lyophilic magnetic particles and a resin surrounded by a resin wall to form microcapsules. Colorants such as pigments or dyes may be included in the wall forming resin or the toner. The magnetic particles are rendered lyophilic by treatment with a titanate or silane coupling agent. The coupling agent is said to uniformly disperse the particles in the binder resin and firmly bond the magnetic particle to the resin.

BRIEF DESCRIPTION OF THE INVENTION

Liquids, oils and especially cosmetic emollient oils generally can be encapsulated by conventional procedures such as shown in U.S. Pat. No. 3,516,941. However, even with careful control of the shear forces in the reaction vessel, the capsules tend to be too small for many commercial applications, particularly in cosmetic applications. The capsules are too difficult to rupture and the broken capsule particles are too small to provide any mildly abrasive benefits.

It has been found that the addition of soluble polymeric materials to the oils enables them to form larger capsules without destroying the properties of the oils. In fact, the polymer also tends to aid the oil in adhering to the surface of skin and penetrating at a more controlled rate over a longer period of time.

It has been found that larger capsules containing cosmetic ingredients can be dispersed in carrying media and provide additional activity including mild cleaning abrasion.

DETAILED DESCRIPTION OF THE INVENTION

In accordance with the present invention, microcapsules are prepared by polymerization such as in situ aminoplast polymerization. The techniques disclosed, generally referred to as an in situ polymerization reaction, yield, for example, an aminoplast resin capsule wall material. In the process, a liquid or oil such as a cosmetic emollient oil phase with a polymeric material dissolved therein is dispersed in an aqueous phase containing the aminoplast resin precursors by applying shear agitation. Addition of an acid catalyst initiates the polycondensation of the aminoplast precursors, resulting in the deposition of the aminoplast resin about the dispersed droplets of the oil phase, producing the microcapsules.

Typical cosmetic emollient oils are organic liquids with viscosities between 2 and 150 cp at 20° C., preferably between 2 and 100 cp. The oils preferably have molecular weights in excess of 100, more preferably in excess of 125 and most preferably between 125 and 500. Examples of commercial oils used as cosmetic emollient oils include mineral oil, castor oil, vegetable oil, corn oil, peanut oil, jojoba oil, 2-ethylhexyl oxystearate (and other alkyl oxystearates), acetylated lanolin alcohol, alkyl palmitates such as isopropyl palmitate, 2-ethylhexyl palmitate, glyceryl triacetates, disopropyl adipate, dioctyl adipate (and other alkyl adipates), isopropyl myristate, $C_{12}$ to $C_{15}$ alcohol benzoates, and the like.

The polymeric additive must be dispersible or soluble in the oil so as to increase its viscosity. These materials are preferably polymers even though waxy substances may be used although with less desirable results. The polymers should be oleophilic to be wetted or soluble in the oil. Examples of preferred polymers include polyolefins, polystyrene, polybutadiene, graft or block polymers of these materials such as a polystyrene-polybutadiene-polystyrene block copolymer, polyacrylates, natural rubber (not heavily vulcanized), polyisoprene, polyisobutylene, cellulose acetate esters such as cellulose acetate butyrate and cellulose acetate proprionate, and the like. It has been found in the practice of the present invention that the increase in viscosity in the oil causes an increase in the average size of the microcapsules. This has not previously been reported.

The process of the present invention utilizes the addition of viscosity increasing materials selected from the group consisting of particulates (e.g., clays and polymeric particles), waxes, and polymeric additives to liquids and oils such as cosmetic emollient oils to increase their viscosity and then using the higher viscosity oil mixtures or solutions in a microencapsulation process to produce particles of a larger size than would ordinarily be formed in encapsulation of the cosmetic emollient oil without additives under identical encapsulation reaction conditions. Polymeric additives are especially preferred because they are more consistent and repeatable in their performance and because they hold the oil better on the skin. These oils with increased viscosity are particularly beneficial in encapsulation processes where shear forces are used to maintain a dispersed phase of oil in the reaction vessel.

The shell material of the capsule may be any of the various materials known to be useful in forming capsules such as organic polymers, particularly phenolic-aldehydes, urea-aldehydes, acrylic polymers, addition polymers, condensation polymers, natural resins such as gelatin and agar-agar, and any of the other many well-known capsule making materials. The capsules are preferably between 50 and 2000 microns in diameter, more preferably between 100 and 1800 microns and most preferably between 200 and 1500 microns. Preferably they having a loading of (emollient and polymer)/(shell) at least 2:1 and preferably between 3:1 and 10:1.

Additional additives such as perfumes, pigments, vitamins, sunscreens, insect repellants and even medication may be added to the oil/polymer mixture, blended with the capsules, or used independently from the oils. These additives, particularly when blended with the capsules after they have been made, may be dispersed in a cream, oil, powder, pancake or other media as a carrier for the capsules. In such media, the capsules would usually constitute from 2 to 50% by weight of the total cosmetic composition, preferably 3 to 40% by weight of the composition, most preferably between 4 and 20% by weight.

EXAMPLE 1

To 900 grams of a mixture of $C_{12}$-$C_{15}$ alcohol benzoates was added 100 grams of a styrene-butadiene-styrene block copolymer (Kraton ® 1107). The mixture was heated for four hours at 120° C. until the copolymer had dissolved. The thickened oil was encapsulated in a urea-formaldehyde capsule according to the teachings of U.S. Pat. No. 3,516,941 with the shear rate controlled to generate capsules having an average diameter between 300 and 400 microns. These capsules could be rubbed onto the skin, either directly by hand or with a brush applicator and ruptured. The oils would spread evenly on the skin and the broken capsule shells provide a useful, mildly abrasive action on the skin.

EXAMPLE 2

720 grams of a mixture of $c_1$-$C_{15}$ alcohol benzoates were mixed with 80 grams of the block copolymer of Example 1 and heated to 120° C. with stirring until completely dissolved. The solution was cooled to 60° C. and 200 grams of a commercially available bactericide (Irgason ®-300) was added to 790 grams of the solution. This mixture was cooled to 40° C. and 10 grams of fragrance was added with stirring. This solution was then encapsulated according to the procedures of Example 1. The capsules were useful as a directly applied underarm deodorant composition. The capsules could also be blended with a wax or cream to form a composition then could be applied to the underarms. The natural movement of the arms is sufficient to rupture the capsules over a period of time.

EXAMPLE 3

Twenty-five grams of the copolymer of Example 1 were dissolved in 975 grams of 2-ethylhexyl oxystearate. The mixture was heated to 100° C. with stirring and dissolved in the manner described below.

The details of the encapsulation process are as follows:

To a one-liter baffled reactor were charged 379 gm urea-formaldehyde precondensate and 181 gm water. Vigorous mixing was applied and 80.1 gm sodium chloride and 0.53 gm sodium carboxymethyl cellulose were added. To the reactor was then added 250.8 gm of the fill material of Example 1 and precise temperature and mixing speed were applied. Sulfuric acid catalyst was added to achieve a pH of 2.5. This condition was held for two hours followed by an increase in temperature to 140° F. for 2 hours. The reaction was cooled to room temperature and neutralized to a pH of 8.0. The resulting capsules were filtered, washed, and dried. The excellent quality capsules were determined to have a median size of 354 microns.

To a one liter baffled reactor were charged 303.2 gm urea-formaldehyde precondensate and 221 gm water. Vigorous mixing was applied, followed by the addition to the reactor of 37.8 gm sodium sulfate and 0.5 gm sodium carboxymethyl cellulose. After achieving solution 297 gm of the fill material, as of Example 2, was added. Precise mixing speed and temperature control were applied followed by the addition of sulfuric acid to pH 2.3. Conditions were held for three hours followed by temperature increase to 140° F. for two hours. The excellent quality capsules having a median size of 61 microns were filtered, washed, and dried to a slightly clumped product.

To a 19 liter baffled reactor were added 7525 gm urea-formaldehyde precondensate and 4000 gm water. Vigorous mixing was applied followed by addition of 1650 gm sodium chloride and 11.0 gm sodium-carboxymethyl cellulose. After obtaining solution 4465 gm of the fill of Example 3 was added. Precise temperature and turbine speed controls were established, followed by addition of dilute hydrochloric acid to a pH of 2.31. This condition was held for two hours followed by a temperature increase to 140° F. for 1.75 hours. The resulting capsules having a median size of 330 microns were of excellent quality.

EXAMPLES 4 and 5

To 215.9 gm of isopropyl palmitate having a measure viscosity of 8 centipoise was added with stirring 71.9 gm of Amoco Indopol H-100 polybutene. The resulting mixture had a measured viscosity of 24 centipoise and was encapsulated.

To 180 ml refined jojoba bean oil having a viscosity of 33 centipoise was added 70 ml Amoco Indopol H-100 polybutene. The resulting mixture had a measured viscosity of 106 centipoise and was encapsulated.

226.1 gm Carnation Mineral Oil and 2.3 gm Kraton 1107 were charged to a wide-mouth jar and were alternately heated on a steam bath and shaken until solution was achieved. The viscosity of the mineral oil increased from its initial value of 19 centipoise to 460 centipoise with the Kraton. This was encapsulated.

The encapsulation process for these oils was the same as described above.

EXAMPLES 6–10

These examples show the effectiveness of viscosity increasing additives in generating larger capsule shells under otherwise identical reaction conditions.

EXAMPLE 6

To a one liter baffled reactor were charged 379 gm urea-formaldehyde precondensate and 181 gm water. Vigorous mixing was applied and 80.1 gm sodium chloride and 0.53 gm sodium carboxymethyl cellulose were added. To the reactor was then added 250.8 gm of the fill material described in Example 1 and precise temperature and mixing speed were applied. Sulfuric acid catalyst was added to achieve a pH of 2.5. This condition was held for two hours followed by an increase in temperature to 140° F. for two hours. The reaction was cooled to room temperature and neutralized to a pH of 8.0. The resulting capsules were filtered, washed, and dried. The excellent quality capsules were determined to have a median size of 354 microns. A similarly-run encapsulation reaction using the unviscofied fill material yielded a median capsule size of 155 microns.

EXAMPLE 7

To a one liter baffled reactor were charged 303.2 gm urea-formaldehyde precondensate and 221 gm water. Vigorous mixing was applied followed by addition to the reactor of 37.8 gm sodium sulfate and 0.5 gm sodium carboxymethyl cellulose. After achieving solution, 297 gm of the fill material as described in Example 2 was added. Precise mixing speed and temperature control were applied followed by addition of sulfuric acid to pH 2.3. Conditions were held for three hours followed by temperature increase to 140° F. for two hours. The excellent quality capsules having a median size of 61 microns were filtered, washed, and dried to a slightly clumped product. Capsules similarly prepared using unviscofied fill had a median size of 32 microns.

EXAMPLE 8

To a 19 liter baffled reactor were added 7525 gm urea-formaldehyde precondensate and 4000 gm water. Vigorous mixing was applied followed by addition of 1650 gm sodium chloride and 11.0 gm sodium carboxymethyl cellulose. After obtaining solution 4465 gm of the fill as described in Example 3 were added. Precise temperature and turbine speed controls were established followed by addition of dilute hydrochloric acid to a pH of 2.31. This condition was held for two hours followed by a temperature increase to 140° F. for 1.75 hours. The resulting capsules having a median size of 330 microns were of excellent quality. Capsules of unviscofied fill from a similar encapsulation reaction had a median size of 145 microns.

EXAMPLE 9

To a one liter baffled reactor were charged 376 gm urea-formaldehyde precondensate and 200 gm water. Vigorous mixing was applied followed by addition to the reactor of 2.5 gm sodium chloride and 0.55 gm sodium carboxymethyl cellulose. After obtaining solution, 216 gm of the mixture as described in Example 4 was added. Precise mixing speed and temperature controls were applied followed by addition of hydrochloric acid to pH of 2.3. This condition was held for two hours followed by an increase in temperature to 40° F for 1.9 hours. The resulting capsules were of excellent quality and had a median size of 186 microns. Unviscofied fill when encapsulated via a similar method yielded capsules having a median size of 146 microns.

EXAMPLE 10

An encapsulation was performed using the procedure as summarized in Example 9 but substituting 250 ml of fill as described in Example 5. The resulting capsules were of excellent quality having a median size of 249 microns. The unviscofied fill yielded capsules of 170 microns median size.

Using the procedure in Example 9 using 250 ml of the mineral oil/Kraton as described in Example 5 as the fill material. The resulting capsules were of varying quality and had an average size of 315 microns.

EXAMPLES 11–13

(a) 352 gm of N,N-diethyl toluamide (DEET) was mixed with heating with 48 gm Kraton ® 1107 until dissolved. The viscosity of the resulting solution measured 91 centipoise; unviscofied DEET measured 17.5 centipoise.

(b) 225 gm of a commercially purchased oil base wood stain having a measured viscosity of 4 centipoise was mixed and heated with 25 gm Kraton ® 1107 until solution was achieved. This mixture had a viscosity of 74 centipoise.

(c) 368 gm of Escalol 507 (2-ethyl hexyl para-dimethylaminobenzoate) was stirred with 32 gm Kraton ® 1107 while being heated on a steam bath until a solution was achieved. The resulting solution has a measured viscosity of 1240 centipoise compared with a viscosity of 60 centipoise for the unviscofied Escalol.

EXAMPLE 11

As in the procedure used in Example 9, using the fill material (a) shown above, capsules with an average diameter of 101 microns were produced. The unviscofied DEET provided capsules of 81 microns under otherwise identical conditions.

EXAMPLE 12

Using the procedures of Example 9 with the fill material (b) described above, capsules with an average diameter of 265 microns were produced. The unviscofied wood stain provided capsules with average diameter of 127 microns under otherwise identical conditions.

EXAMPLE 13

Using the procecure of Example 9 with 250 ml of the Escalol/Kraton as described in (c) above as the fill material, microcapsules were formed. The resulting capsules were of varying quality and had a median volume size of 326 microns; unviscofied fill encapsulated in similar fashion yielded capsules of 165 micron size.

We claim:

1. Microcapsules of encapsulated oil comprising an oil having a polymeric thickener therein which increases the viscosity of said oil by at least 70 cp encapsulated by an aminoplast polymeric shell, said microcapsules having average diameters between 50 and 2000 microns.

2. The microcapsules of claim 1 wherein said polymeric thickening agent is selected from the group consisting of polyolefins, polybutadiene, polystyrene, polyacrylics, gelatin, natural rubber, polyisoprene, cellulose acetate esters and copolymers thereof.

3. The microcapsules of claim 1 having average diameters between 100 and 2000.

4. The microcapsules of claim 3 wherein said oil without polymeric thickeners has a viscosity at 20° C. of between 2 and 150 cp.

5. The microcapsules of claim 4 wherein said oil is a cosmetic oil and the oil plus thickener has a viscosity between 300 and 1500 cp at 20° C.

6. The microcapsules of claim 3 wherein said oil is an emollient oil and is selected from the group consisting of mineral oil, castor oil, jojoba oil, vegetable oil, 2-ethylhexyl oxystearate, $C_{12}$–$C_{15}$ alcohol benzoates, isopropyl palmitate and isopropyl myristate.

7. The microcapsules of claim 6 wherein said polymeric thickening agent is selected from the group consisting of polyolefins, polybutadiene, polystyrene, polyacrylics, gelatin, natural rubber, polyisoprene, cellulose acetate esters and copolymers thereof.

8. The microcapsules of claim 3 wherein said polymeric thickening agent is selected from the group consisting of polyolefins, polybutadiene, polystyrene, polyacrylics, gelatin, natural rubber, polyisoprene, cellulose acetate esters and copolymers thereof.

9. The microcapsules of claim 1 having average diameters between 200 and 1500.

10. The microcapsules of claim 9 wherein said oil without polymeric thickeners has a viscosity at 20° C. of between 2 and 150 cp.

11. The microcapsules of claim 10 wherein said oil is a cosmetic emollient oil and the oil plus thickener has a viscosity between 300 and 1500 cp at 20° C.

12. The microcapsules of claim 9 wherein said oil is an emollient oil and is selected from the group consisting of mineral oil, castor oil, jojoba oil, vegetable oil, 2-ethylhexyl oxystearate, $C_{12}$–$C_{15}$ alcohol benzoates, isopropyl palmitate and isopropyl myristate.

13. The microcapsules of claim 12 wherein said polymeric thickening agent is selected from the group consisting of polyolefins, polybutadiene, polystyrene, polyacrylics, gelatin, natural rubber, polyisoprene, cellulose acetate esters and copolymers thereof.

14. The microcapsules of claim 9 wherein said polymeric thickening agent is selected from the group consisting of polyolefins, polybutadiene, polystyrene, polyacrylics, gelatin, natural rubber, polyisoprene, cellulose acetate esters and copolymers thereof.

15. The microcapsules of claim 1 wherein said oil without polymeric thickeners has a viscosity at 20° C. of between 2 and 150 cp.

16. The microcapsules of claim 15 wherein said oil is a cosmetic emollient oil and the oil plus thickener has a viscosity between 300 and 15000 cp at 20° C.

17. The microcapsules of claim 1 wherein said oil is an emollient oil and is selected from the group consisting of mineral oil, castor oil, jojoba oil, vegetable oil, 2-ethylhexyl oxystearate, $C_{12}$–$C_{15}$ alcohol benzoates, isopropyl palmitate and isopropyl myristate.

18. The microcapsules of claim 17 wherein said polymeric thickening agent is selected from the group consisting of polyolefins, polybutadiene, polystyrene, polyacrylics, gelatin, natural rubber, polyisoprene, cellulose acetate esters and copolymers thereof.

19. A process for encapsulating oils comprising mixing an oil having a viscosity of between 2 and 150 cp at 20° C. and a molecular weight in excess of 100 with an additive that increases the viscosity of said oil by at least 70 cp and which is dispersible or soluble in said oil, then encapsulating said oil with said additive by condensing an aminoplast resin to produce microcapsules having average diameters of between 50 and 2000 microns.

20. The process of claim 19 wherein said additive comprises a polymer soluble in said oil, and said oil is a cosmetic emollient oil.

21. The process of claim 20 in which the oil and viscosity increasing additive comprise a cosmetic emollient oil phase which is dispersed in an aqueous phase containing resin precursors and the resin precursors are reacted to form a shell about said cosmetic emollient oil phase.

22. The process of claim 19 in which the oil and viscosity increasing additive comprise a hydrophobic oil phase which is dispersed in an aqueous phase containing resin precursors and the resin precursors are reacted to form a shell about said hydrophobic oil phase.

* * * * *